(12) United States Patent
Roth

(10) Patent No.: US 6,331,418 B1
(45) Date of Patent: Dec. 18, 2001

(54) SACCHARIDE COMPOSITIONS, METHODS AND APPARATUS FOR THEIR SYNTHESIS

(75) Inventor: Stephen Roth, Gladwyne, PA (US)

(73) Assignee: Neose Technologies, Inc., Horsham, PA (US)

(*) Notice: Subject to any disclaimer, the term of this patent is extended or adjusted under 35 U.S.C. 154(b) by 0 days.

(21) Appl. No.: 08/480,317

(22) Filed: Jun. 7, 1995

Related U.S. Application Data

(63) Continuation of application No. 08/163,534, filed on Dec. 9, 1993, now abandoned, which is a continuation of application No. 07/955,687, filed on Oct. 2, 1992, now Pat. No. 5,288,637, which is a continuation of application No. 07/683,810, filed on Apr. 11, 1991, now Pat. No. 5,180,674, which is a continuation-in-part of application No. 07/509,560, filed on Apr. 16, 1990, now abandoned.

(51) Int. Cl.$^7$ .............................. C12P 19/18; C12P 19/12

(52) U.S. Cl. ............................ 435/97; 435/72; 435/100; 435/101; 435/105; 435/193; 435/815

(58) Field of Search ............................ 435/72, 100, 97, 435/101, 105, 193, 815

(56) References Cited

U.S. PATENT DOCUMENTS

| | | | |
|---|---|---|---|
| 3,666,627 | 5/1972 | Messing | 435/176 |
| 3,930,950 | 1/1976 | Royer | 435/176 |
| 4,150,116 | 4/1979 | Taubman et al. | |
| 4,184,917 | 1/1980 | Dorner et al. | 435/68.1 |
| 4,219,571 | 8/1980 | Miyake | 426/48 |
| 4,250,262 | 2/1981 | Taubman et al. | 435/193 |
| 4,264,227 | 4/1981 | Iwasaki | 401/94 |
| 4,359,531 | 11/1982 | Bucke et al. | 426/536 |
| 4,386,158 | 5/1983 | Shimizu et al. | 435/97 |
| 4,451,566 * | 5/1984 | Spencer | 435/162 |
| 4,537,763 | 8/1985 | Miyake et al. | 435/97 |
| 4,557,927 | 12/1985 | Miyake et al. | 455/78 |
| 4,569,909 | 2/1986 | Seno et al. | 435/89 |
| 4,590,160 | 5/1986 | Nishihashi et al. | 435/78 |
| 4,594,321 | 6/1986 | Fujishima et al. | 435/89 |
| 4,617,269 | 10/1986 | Rathbone et al. | 435/97 |
| 4,621,137 | 11/1986 | Miyake et al. | 435/97 |
| 4,624,919 | 11/1986 | Kokusho et al. | 435/74 |

(List continued on next page.)

FOREIGN PATENT DOCUMENTS

| | | | |
|---|---|---|---|
| 146890 * | 6/1989 | (JP) | C07H/3/04 |
| 84850211.8 | 2/1985 | (WO) | |
| WO 89/09275 | 10/1989 | (WO) | |

(List continued on next page.)

OTHER PUBLICATIONS

Toone et al, Tetrahedron 45(17): 5365–5422 (1989).*
Eijnden et al, Jour. Biol. Chem. 258(6): 3345–3347 (1983).*
Kitagawa et al, Jour. Biol. Chem. 265(9): 4859–4862 (1990).*
Chemical Abstracts 74(17): 29979q (1971).*
Paal, Carbohydrate Research, vol. 137, pp. 39–62, (1985).*
Armstrong, Phil. Bus. J., (Dec. 9–15, 1991) 2 pp.
Appert et al., 1986, Biochem. Biophys. Res. Comm. 139:163–168.
Auge, et al., *Carbohydrate Research,* 151, pp. 147–156 (1986).
Auge et al., *Carbohydrate Research,* 193, pp. 288–293 (1989).
Auge et al., *Carbohydrate Research,* 200, pp. 257–268 (1990).
Barker et al., 1972, J. of Biol. Chem. 247:7135–7147.
Beanau et al., 1990, J. Histochem. and Cytochem. 38:23–30.
Borman, 1992, "Race Is On To Develop Sugar–Based Anti–inflammatory, Antitumor Drugs," Chemical & Engineering News, Dec. 7, 1992, pp. 25–28.
Borman, 1993, "Glycotechnology Drugs Begin To Emerge from the Lab," Chemical & Engineering News, Jun. 28, 1993, pp. 27–34.

(List continued on next page.)

*Primary Examiner*—T. D. Wessendorf
(74) *Attorney, Agent, or Firm*—Pennie & Edmonds LLP

(57) ABSTRACT

A method for preparing saccharide compositions which is reiterative and includes the following three steps.

(i) A glycosyltransferase capable of transferring a preselected saccharide unit to an acceptor moiety is isolated by contacting the acceptor moiety with a mixture suspected of containing the glycosyltransferase under conditions effective to bind the acceptor moiety and the glycosyltransferase and thereby isolate the glycosyltransferase. The acceptor moiety is a protein, a glycoprotein, a lipid, a glycolipid, or a carbohydrate.

(ii) The isolated glycosyltransferase is then used to catalyze the bond between the acceptor moiety and the preselected saccharide unit.

(iii) Steps (i) and (ii) are repeated a plurality of times with the intermediate product obtained in the first iteration of the method being used as the acceptor moiety of the second iteration.

23 Claims, 1 Drawing Sheet

U.S. PATENT DOCUMENTS

| | | | |
|---|---|---|---|
| 4,670,387 | 6/1987 | Bucke et al. | 435/97 |
| 4,678,747 | 7/1987 | Lloyd et al. | 435/7 |
| 4,683,198 | 7/1987 | Ishikawa et al. | 426/22 |
| 4,683,297 | 7/1987 | Yanami | 536/18.6 |
| 4,693,974 | 9/1987 | Schwengers et al. | 435/97 |
| 4,757,012 | 7/1988 | Estell et al. . | |
| 4,770,994 | 9/1988 | Rittenhouse | 435/7.23 |
| 4,782,019 | 11/1988 | Kokusho et al. | 435/89 |
| 4,818,816 | 4/1989 | Petitou et al. . | |
| 4,835,105 | 5/1989 | Seres et al. | 435/97 |
| 4,835,264 | 5/1989 | Liav et al. | 536/4.1 |
| 4,849,356 | 7/1989 | Van Dooren et al. | 435/183 |
| 4,851,517 | 7/1989 | Feder et al. . | |
| 4,855,128 | 8/1989 | Lynch et al. . | |
| 4,859,590 | 8/1989 | Thiem et al. | 435/97 |
| 4,865,976 | 9/1989 | Rohrback | 435/107 |
| 4,868,104 | 9/1989 | Kurn et al. . | |
| 4,876,195 | 10/1989 | Shirafuji et al. . | |
| 4,900,822 | 2/1990 | Von der Eltz . | |
| 4,912,093 | 3/1990 | Michaeli . | |
| 4,918,009 | 4/1990 | Nilsson | 435/73 |
| 4,925,796 * | 5/1990 | Bergh et al. | 435/97 |
| 4,931,389 | 6/1990 | Kobayashi et al. | 435/95 |
| 4,943,630 | 7/1990 | Jacquinet et al. . | |
| 4,957,860 * | 9/1990 | Kan et al. | 435/101 |
| 5,047,335 | 9/1991 | Paulson et al. . | |
| 5,180,674 * | 1/1993 | Roth | 435/288 |
| 5,288,637 * | 2/1994 | Roth | 435/288 |
| 5,308,460 * | 5/1994 | Mazid et al. | 204/180.1 |
| 5,874,261 | 2/1999 | Roth . | |

FOREIGN PATENT DOCUMENTS

| | | |
|---|---|---|
| 8909725 * | 10/1989 | (WO) . |
| WO 90/05304 | 5/1990 | (WO) . |
| WO 91/12340 | 8/1991 | |

OTHER PUBLICATIONS

Borman, 1993, "Patent Grants Broad Protection To Enzyamatic Carbohydrate Synthesis," Chemical & Engineering News, Mar. 29, 1993, pp. 24–27.
Cartron et al., 1976, FEBS Lett., 67:143–148.
Closs et al., 1982, J. Org. Chem. 47:5416–5418.
Cote et al., 1990, Chem. Abstr., vol. 113, Abstract No. 113:187372q.
Creeger et al., 1979, J. Biol. Chem. 254:804–810.
Demers et al., 1985, J. of Appl. Biochem. 7:122–125.
Elices et al., 1987, Arch. Biochem. Biophys. 254:329–341.
Ernst, et al., 1989, J. Biol. Chem. 264:3436–3447.
Furukawa et al., 1985, Biochem. J. 227:573–582.
Ichikawa et al., 1992, "Enzyme–Catalyzed Oligosaccharide Synthesis," Anal. Biochem. 202:215–238.
Katsumi et al., 1989, Chem. Abstr. vol. 111, Abst. No. 111:152000y, p.565.
Kirk–Othmer, 1980, Encyclopedia of Chemical Technology, 3rd Ed., vol. 9, p. 148–172, John Wiley & Sons.
Kitahata, 1989, Chem. Abstr. vol. 111, Abst. No. 111:93061u, p. 355.
Kitahata, 1990, Chem. Abstr. vol. 113, Abstr. vol. 113, Abst. No. 113:170336h, p. 567.
Larsen, et al., 1989, Proc. Natl. Acad. Sci. USA, 86:8227–8231.
Narimatsu et al., 1986, Proc. Natl. Acad. Sci. USA 83:4720–4724.
Nilsson, 1989, Immunochem. vol. 110, Abstr. 110:6111y, p. 581.
Nunez et al., 1980, Biochemistry 19:489–495.
Palcic et al., 1987, Carbohydrate Res. 159:315–324.
Palcic et al., 1989, Carbohydrate Res. 190:1–11.
Parodi et al., 1978, Biomedicine 28:9–13.
(WO) .
Pollak et al., 1980, J. Am. Chem. Soc. 102:6324–6336.
Rajan et al., 1989, J. Biol. Chem. 264:11158–11167.
Rosevear et al., 1982, "Synthesis and Solution Conformation of the Type 2 Blood Group Oligosaccharide αLFus (1–2)βDGal(1→4)βDGlcNAC," Biochemistry 21:1421–1431.
Roth et al., 1983, Exper. Cell Res. 143:217–225.
Sabesan et al., 1986, J. A. Chem. Soc. 108:2068–2080.
Sadler et al., 1982, Meth. in Enzymol. 83:458–493.
Schaal et al., 1990, Glycoconjugate J. 7:475.
Sheares et al., 1983, J. Biol. Chem. 258:9893–9898.
Suganuma et al., 1987, J. Biochem. 102:665–671.
Theim et al., 1986, Angew. Chem. Int. Ed. Engl. 25:1096–1097.
Toone et al., 1989 Tetrahedron 45:5365–5422.
Van Brunt, "Abbott Invests $17M in Neose", Bioworld Today, vol. 4, No. 30, p. 1, Feb. 12, 1993.
van den Eijnden et al., 1983, "Novikoff Ascites Tumor Cells Contain N–Actelyllactosamide β1→3 and β1→6 N–Acetyl-glucosaminyltransferase Activity," J. Biol. Chem. 258:3435–3437 Check Pages.
Weinstein et al., 1982, J. of Biol. Chem. 257:13835–13844.
Wong, 1989, Science 244:1145–1152.
Zehavi et al., 1983, Carbohydrate Res. 124:23–34.
Zehavi et al., 1984, Carbohydrate Res. 128:160–164.
Zehavi et al., 1984, Carbohydrate Res. 133:339–342.
Zopf and Ohlson, 1990, "Weak–affinity Chromatography", Nature 346:87–88.
1988 FASEB Abstract Form (1p.)w.3 Abstracts Submitted to UCLA Glycobiology Symposium (3 pp.).
"A Drug Collaboration," Philadelphia Enquirer, Feb. 12, 1993.
The Merck Index, 10th ed., 1983, index No. 8320.
U.S. application No., 08/484,885, Roth, filed Jun. 7, 1995.

* cited by examiner

SACCHARIDE COMPOSITIONS, METHODS AND APPARATUS FOR THEIR SYNTHESIS

RELATED APPLICATION

This application is a continuation of U.S. application Ser. No. 08/163,534 filed Dec. 9, 1993, now abandoned, which is a continuation of U.S. application Ser. No. 07/955,687 filed Oct. 2, 1992, now U.S. Pat. No. 5,288,637, which is a continuation of U.S. application Ser. No. 07/683,810 filed Apr. 11, 1991, now U.S. Pat. No. 5,180,674 which is a continuation-in-part of U.S. application Ser. No. 07/509,560 filed Apr. 16, 1990, now abandoned. This application also relates to subject matter disclosed in U.S. application No. 07/241,012 filed Sep. 2. 1988, now abandoned, which is incorporated herein by reference in its entirety.

GOVERNMENT SUPPORT

Portions of this invention were supported by National Science Foundation Grant DCB8817883.

BACKGROUND OF THE INVENTION

1. Field of the Invention

This invention relates to saccharide compositions such as, for example, oligosaccharides, polysaccharides, glycolipids, and glycoproteins. More specifically, this invention relates to processes for preparing these and other saccharide compositions by enzymatic techniques.

2. Discussion of the Background

The term "carbohydrate" embraces a wide variety of chemical compounds having the general formula $(CH_2O)_n$, such as monosaccharides, disaccharides, oligosaccharides and polysaccharides. Oligosaccharides are chains composed of saccharide units, which are alternatively known as sugars. These saccharide units can be arranged in any order and the linkage between two saccharide units can occur in many of approximately ten different ways. As a result, the number of different possible stereoisomeric oligosaccharide chains is enormous.

Of all the biological polymer families, oligosaccharides and polysaccharides have been the least well studied, due in considerable part to the difficulty of sequencing and synthesizing their often complex sugar chains. Although the syntheses of oligonucleotides and polypeptides are well developed, there is currently no generally applicable synthetic technique for synthesizing oligosaccharides.

Numerous classical techniques for the synthesis of carbohydrates have been developed, but these techniques suffer the difficulty of requiring selective protection and deprotection. Organic synthesis of oligosaccharides is further hampered by the lability of many glycosidic bonds, difficulties in achieving regioselective sugar coupling, and generally low synthetic yields. These difficulties, together with the difficulties of isolating and purifying carbohydrates and of analyzing their structures, has made this area of chemistry a most demanding one.

Much research effort has been devoted to carbohydrates and molecules comprising carbohydrate fragments, such as glycolipids and glycoproteins. Research interest in such moieties has been largely due to the recognition that interactions between proteins and carbohydrates are involved in a wide array of biological recognition events, including fertilization, molecular targeting, intercellular recognition, and viral, bacterial, and fungal pathogenesis. It is now widely appreciated that the oligosaccharide portions of glycoproteins and glycolipids mediate recognition between cells and cells, between cells and ligands, between cells and the extracellular matrix, and between cells and pathogens.

These recognition phenomena can likely be inhibited by oligosaccharides having the same sugar sequence and stereochemistry found on the active portion of a glycoprotein or glycolipid involved in cell recognition. The oligosaccharides are believed to compete with the glycoproteins and glycolipids for binding sites on receptor proteins. For example, the disaccharide galactosyl β 1-4 N-acetylglucosamine is believed to be one component of the glycoproteins which interact with receptors in the plasma membrane of liver cell. Thus, to the extent that they compete with potentially harmful moieties for cellular binding sites, oligosaccharides and other saccharide compositions have the potential to open new horizons in pharmacology, diagnosis, and therapeutics.

There has been relatively little effort to test oligosaccharides as therapeutic agents for human or animal diseases, however, as methods for the synthesis of oligosaccharides have been unavailable as noted above. Limited types of small oligosaccharides can be custom-synthesized by organic chemical methods, but the cost for such compounds is typically very high. In addition, it is very difficult to synthesize oligosaccharides stereospecifically and the addition of some sugars, such as sialic acid and fucose, has not been effectively accomplished because of the extreme lability of their bonds. Improved, generally applicable methods for oligosaccharide synthesis are desired for the production of large amounts of widely varying oligosaccharides for pharmacology and therapeutics.

For certain applications, enzymes have been targeted for use in organic synthesis as one alternative to more traditional techniques. For example, enzymes have been used as catalysts in organic synthesis; the value of synthetic enzymatic reactions in such areas as rate acceleration and stereoselectivity has been demonstrated. Additionally, techniques are now available for low cost production of some enzymes and for alteration of their properties.

The use of enzymes as catalysts for the synthesis of carbohydrates has been proposed, but to date enzyme-based techniques have not been found which are useful for the general synthesis of oligosaccharides and other complex carbohydrates in significant amounts. It has been recognized that a major limiting factor to the use of enzymes as catalysts in carbohydrate synthesis is the very limited current availability of the broad range of enzymes required to accomplish carbohydrate synthesis. See Toone et al, *Tetrahedron Reports* (1990)(45)17:5365–5422.

In mammalian systems, eight monosaccharides activated in the form of nucleoside mono- and diphosphate sugars provide the building blocks for most oligosaccharides: UDP-Glc, UDP-GlcUA, UDP-GlcNAC, UDP-Gal, UDP-GalNAc, GGP-Man, GDP-Fuc and CMP-NeuAc. These are the intermediates of the Leloir pathway. A much larger number of sugars (e.g., xylose, arabinose) and oligosaccharides are present in microorganisms and plants.

Two groups of enzymes are associated with the in vivo synthesis of oligosaccharides. The enzymes of the Leloir pathway is the largest group. These enzymes transfer sugars activated as sugar nucleoside phosphates to a growing oligosaccharide chain. Non-Leloir pathway enzymes transfer carbohydrate units activated as sugar phosphates, but not as sugar nucleoside phosphates.

Two strategies have been proposed for the enzyme-catalyzed in vitro synthesis of oligosaccharides. See Toone et al, supra. The first strategy proposes to use glycosyltransferases. The second proposes to use glycosidases or glycosyl hydrolases.

Glycosyltransferases catalyze the addition of activated sugars, in a stepwise fashion, to a protein or lipid or to the non-reducing end of a growing oligosaccharide. A very large number of glycosyltransferases appear to be necessary to synthesize carbohydrates. Each NDP-sugar residue requires a distinct class of glycosyltransferases and each of the more than one hundred glycosyltransferases identified to date appears to catalyze the formation of a unique glycidic linkage. To date, the exact details of the specificity of the glycosyltransferases are not known. It is not clear, for example, what sequence of carbohydrates is recognized by most of these enzymes.

Enzymes of the Leloir pathway have begun to find application to the synthesis of oligosaccharides. Two elements are required for the success of such an approach. The sugar nucleoside phosphate must be available at practical cost and the glycosyltransferase must be available. The first issue is resolved for most common NDP-sugars, including those important in mammalian biosynthesis. The problem in this technology however resides with the second issue. To date, only a very small number of glycosyltransferases are available. Access to these types of enzymes has been the single limiting factor to this type of carbohydrate synthesis.

It has been reported that most glycosyltransferases are difficult to isolate, particularly from mammalian source. This is because these proteins are present in low concentrations and are membrane-bound. Further, although a few glycosyltransferases have been immobilized, these enzymes have been reported to be unstable. To date only a very small number of glycosyltransferases are available from commercial sources, and these materials are expensive.

Much hope has therefore been put on future developments in genetic engineering (i.e., cloning) of enzymes, particularly since several glycosyltransferases have already been cloned, including galacto-, fucosyl-, and sialyltransferases. It is hoped that future advances in cloning techniques will speed the cloning of other glycosyltransferases and enhance their stability.

Accordingly, in light of their potential uses and the difficulty or impossibility to obtain them in sufficient quantities, there exists a long-felt need for general synthetic methods for the production of oligosaccharides, polysaccharides, glycoproteins, glycolipids, and similar species in an efficient, cost effective, stereospecific, and generally applicable manner.

SUMMARY OF THE INVENTION

It is an object of the present invention to provide saccharide compositions, particularly oligosaccharides, polysaccharides and chemical moieties which comprise oligosaccharide units.

It is another object of this invention to provide a wide variety of saccharide compositions, including those not found in nature.

It is a further object of this invention to provide saccharide compositions useful in mitigating the effects of human or animal diseases.

It is yet another object of this invention to provide improved processes for preparing saccharide compositions.

It is a further object of this invention to provide enzymatic processes for preparing saccharide compositions.

It is still another object of this invention to provide processes for obtaining enzymes useful in synthesizing saccharide compositions.

It is still another object of this invention to provide an apparatus useful for the synthesis of saccharide compositions in accordance with the present invention.

These and other objects are achieved by the present invention, which provides enzymatic processes for preparing oligosaccharides, polysaccharides, glycolipids, glycoproteins, and other saccharide compositions. These processes involve the enzyme-facilitated transfer of a preselected saccharide unit from a donor moiety to an acceptor moiety. Saccharide compositions having a plurality of saccharide units are preferably prepared by appending the saccharide units in stepwise fashion to acceptor moieties which are themselves saccharide compositions prepared in accordance with this invention.

Accordingly, methods for preparing saccharide compositions are provided comprising the steps of providing an acceptor moiety and contacting the acceptor moiety with a glycosyltransferase. The glycosyltransferase is prepared so as to be specific for the acceptor moiety and capable of transferring a saccharide unit to the acceptor moiety. This method of the present invention is performed a plurality of times such that the product of the first iteration becomes the acceptor moiety for a second iteration, and so forth.

DETAILED DESCRIPTION OF THE PREFERRED EMBODIMENTS

Figure 1:
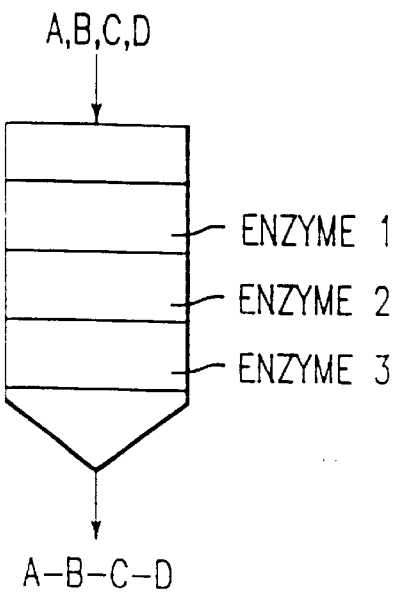
FIGS. 1, 2 and 3 illustrate apparatuses suitable for use in the glycosyltransferase catalyzed synthesis of saccharide composition in accordance with the invention.

As employed herein, the term "saccharide composition" is intended to include any chemical moiety having a saccharide unit within its structure. Sugars, carbohydrates, saccharides, monosaccharides, oligosaccharides, polysaccharides glycoproteins, and glycolipids provide examples of saccharide compositions. Mixtures and solutions comprising such moieties are also saccharide compositions.

Saccharide compositions are prepared according to this invention by the enzyme facilitated transfer of saccharide units from donor moieties to acceptor moieties. It will be appreciated that such transfer occurs upon contacting the acceptor and donor moieties with a glycosyltransferase, and typically results in covalently bonding of the acceptor moiety and the saccharide unit stereoselectively, that is, in but one stereoisomeric form.

The saccharide compositions prepared in accordance with this invention are believed to find wide utility in diagnostics, therapeutics, and pharmacological applications. Once the sugar sequence of a desired target saccharide composition has been determined by conventional methods, a retrosynthetic analysis is generally performed to determine an appropriate synthetic scheme for the saccharide composition. Such a synthetic scheme preferably identifies the particular donor moieties, acceptor moieties, and glycosyltransferases necessary to yield the desired saccharide composition.

Instead of relying on future developments in genetic engineering to provide the numerous glycosyltransferases required for carbohydrate synthesis, the present invention relies on the very different approach as follows. In the synthesis of a saccharide composition in accordance with the invention, a preselected saccharide unit is first enzymatically attached to an initial acceptor moiety, i.e., a protein, a glycoprotein, a lipid, a glycolipid, or a carbohydrate starting material. This is followed by enzymatically attaching preselected saccharide units to the product obtained in a stepwise fashion thereby forming the saccharide composition.

With the attachment of each preselected saccharide unit one obtains an intermediate product. The present invention is based on the inventor's discovery that the starting material of the synthesis (i.e., the protein, glycoprotein, lipid, glycolipid or carbohydrate) and each intermediate product formed in the synthesis can be advantageously used to obtain, for each corresponding step of the synthesis, a glycosyltransferase specific to catalyze the attachment of the next intermediate product in the synthesis of the target saccharide composition.

Thus, in accordance with the invention, the glycosyltransferase needed for any given step is isolated with the intermediate product (the acceptor moiety) and used to attach to the acceptor moiety the next saccharide unit necessary for construction of the target carbohydrate molecule. In accordance with the present invention, this process is repeated, with each iteration (time) yielding the particular glycosyltransferase required to attach the next saccharide unit onto the growing molecule being isolated, until the target carbohydrate molecule is obtained.

Also provided by the invention are reaction conditions and co-reagents as may be necessary and sufficient to effect the covalent bonding of the saccharide unit to the acceptor moiety.

In accordance with preferred embodiments, the acceptor moiety may be a protein, glycoprotein, lipid, glycolipid, or carbohydrate, such as a monosaccharide, disaccharide, oligosaccharide, or polysaccharide. In accordance with other preferred embodiments, the glycosyltransferase is attached to a solid support.

The present methods are capable of stereospecific attachment of the saccharide unit to the acceptor moiety. In general, it is preferred to employ saccharide nucleotides as donor moieties. Uridine, guanosine, and cytidine phosphate materials terminated by the saccharide units to be donated preferably comprise the donor moieties.

The present invention thus also provides means for preparing a glycosyltransferase specific for a particular acceptor moiety and capable of transferring a preselected saccharide unit to the acceptor moiety. Such methods comprise contacting the acceptor moiety with a mixture suspected to contain a plurality of glycosyltransferases under conditions effective to bind the acceptor moiety and the glycosyltransferase specific for the acceptor moiety. The resulting, bound glycosyltransferase is subsequently isolated. It is preferred that the glycosyltransferase be sequenced and that the glycosyltransferase be produced in enhanced quantities by genetic engineering techniques.

The mixture suspected to contain a glycosyltransferase of interest may be identified as follows. For the most common glycosidic linkages, the glycosyltransferase activities have been described in publications. This is largely true for compounds like milk oligosaccharides, or the carbohydrate moieties of typical (i.e., prevalent) glycoproteins and glycolipids. For less well described linkages, one may first look to the tissue, organ, foodstuff organism, in which the linkage is found. Generally, if the linkage is found in a particular source, the enzyme that made the linkage is also present in the source.

If one is presented only with a saccharide structure, and not a source, one can then test examples of organisms that are likely to contain such a saccharide structure using the most sensitive screening assay available. For example, if the compound contained iduronic acid, N-acetylgalactosamine and N-acetylglucosamine, one would test vertebrate connective tissue. If the target compound contain abequose, one would test bacteria and plants for the presence of the appropriate glycosyltransferase.

Various assays for detecting glycosyltransferases which can be used in accordance with the invention have been published. The following are illustrative. Furukawa et al, *Biochem. J.*, (1985) 227:573–582 describe a borate-impregnated paper electrophoresis assay and a fluorescence assay (FIG. 6) developed by the inventor. Roth et al, *Exp'l Cell Research* (1983) 143:217–225 describe application of the borate assay to glucuronyl transferases, previously assayed calorimetrically. Benau et al, *J. Histochem. Cytochem.* (1990) 38(1):23–30 describe a histochemical assay based on the reduction, by NADH, of diazonium salts.

Once a source for the glycosyltransferase of interest has been found, the source is homogenized. The enzyme is purified from homogenate by affinity chromatography using the acceptor moiety as the affinity ligand. That is, the homogenate is is passed over a solid matrix having immobilized thereon the acceptor moiety under conditions which cause the glycosyltransferase to bind to the acceptor moiety. The solid support matrix having the glycosyltransferase bound thereto is then washed. This is followed by an elution step in which the glycosyltransferase is desorbed from the solid support matrix and collected. As known, the absorbed glycosyltransferase may be eluted, for example, by passing an aqueous salt (e.g. NaCl) solution over the solid support matrix.

In actual practice of the invention, the "enzyme" purified from the homogenate by affinity chromatography and which is used to attach a preselected saccharide unit onto the acceptor moiety comprises a mixture of various glycosyltransferases which have been purified away from other extraneous biological material present in the homogenate which includes enzymes which can interfere with the desired activity of the purified glycosyltransferases. Thus, the glycosyltransferases used in accordance with the present invention are frequently a mixture of various "glycosyltransferase". If desired, this material may be further purified with a single purified glycosyltransferase being isolated and used in the process of the present invention, but such further purification is generally not necessary.

In accordance with the present invention, an acceptor moiety is provided which is capable of being covalently bound to a preselected saccharide unit. Representative acceptor moieties include proteins, glycoproteins, lipids, glycolipids and carbohydrates. It will be appreciated that acceptor moieties are preferred to the extent that they are present as a structural component of a saccharide-composition of interest. For example, in preparing a saccharide composition such as N-acetylneuraminyl α 2-3 galactosyl β 1-4 N-acetylglucosamine, preferred acceptor moieties would be N-acetylglucosamine and galactosyl β 1-4 N-acetylglucosamine. It will likewise be appreciated that where an acceptor moiety is terminated by a saccharide unit, subsequent saccharide units will typically be covalently bound to the nonreducing terminus of the terminal saccharide.

The saccharide unit to be transferred to an acceptor moiety is provided by a donor moiety for the saccharide unit. A donor moiety according to this invention includes the saccharide unit to be transferred and is capable of providing that saccharide unit to the acceptor moiety when contacted by the acceptor moiety and the appropriate glycosyltransferase. Preferred donor moieties are saccharide nucleotides, such as saccharide-terminated uridine phosphates, saccharide-terminated guanosine phosphates, and saccharide-terminated cytidine phosphates.

It will be appreciated that donor moieties are preferred to be capable of readily providing their component saccharide unit to an acceptor moiety when placed in contact therewith and with a glycosyltransferase. For example, uridine diphosphate galactose is preferred for transferring galactose to N-acetylglucosamine, while cytidine monophosphate N-acetylneuraminic acid is preferred for transferring N-acetylneuraminic acid, a sialic acid, to galactosyl β 1-4 N-acetylglucosamine.

Upon identification of acceptor moieties and donor moieties necessary for the preparation of a saccharide composition, a glycosyltransferase for each acceptor/donor pair should be prepared. Those skilled in the art will appreciate that a glycosyltransferase may be broadly defined as an enzyme which facilitates the transfer of a saccharide unit from one chemical moiety (here defined as a donor) to another (here defined as an acceptor) and which is named phenomenologically according to the saccharide unit it transfers. Thus, galactosyltransferase transfers galactose, while fucosyltransferase transfers fucose.

Glycosyltransferases according to this invention are those able to effect the transfer of a predetermined saccharide unit to an acceptor moiety. Glycosyltransferases are preferably specific for an acceptor moiety or at least some significant, active, or exposed portion thereof. specificity is manifested for a glycosyltransferase by its tendency to bind with a particularly sequenced portion of an acceptor moiety when placed in contact or close proximity therewith and to effect the transfer of a particular saccharide unit to that acceptor moiety.

Currently, glycosyltransferases are available only from natural sources and, as a result, are somewhat limited in number. It will be appreciated that known glycosyltransferases are only capable of effecting saccharide unit transfers which are highly specific, both in terms of the chemical identity of the saccharide unit transferred and the stereochemistry of its subsequent attachment to the acceptor moiety. For example, it is known that one N-acetylneuraminyltransferase can effect the transfer of N-acetylneuraminic acid to an acceptor moiety bearing only a galactose unit to produce a saccharide composition having an α 2-3 linkage between the N-acetylneuraminic acid unit and the galactose unit.

Thus, the invention permits construction of sugar linkages found in nature. For example, the linkage of galactose α 1-2 to N-acetylneuraminic acid, which has not been found in nature, cannot presently be effected. The methods disclosed herein are, however, applicable to any type of glycosyltransferase which may become available.

While the behavior of a number of glycosyltransferases is known, most glycosyltransferases are currently not fully characterized. The present invention, however, provides methods by which all glycosyltransferases amenable to its practice may be identified and prepared. It has now been found that an acceptor moiety can be used as an affinity chromatographic tool to isolate enzymes that can be used to transfer particular saccharide units and, thus, synthesize other glycosides.

In a preferred embodiment, an acceptor moiety is immobilized as, for example, on a solid support. It will be appreciated that the term "solid support" includes semi-solid supports as well. Once immobilized, the acceptor moiety is contacted with a mixture suspected to contain glycosyltransferases, such as one comprising naturally-occurring cell homogenate. Since an immobilized acceptor moiety will bind an enzyme specific for it, this system is then monitored for acceptor-bound enzyme.

Monitoring for acceptor-bound enzyme may be carried out as follows. The cell homogenate is passed over the immobilized acceptor moiety. This may be achieved, for example, by passing the cell homogenate over a column charged with immobilized acceptor moiety. The column is then washed and the amount of protein which passes through the column charged with immobilized acceptor moiety is monitored. When no more protein is detected, an aqueous salt solution eluant is passed through the column to elute the enzyme. The eluant obtained is then assayed for the presence of glycosyltransferase(s). The assays which can be used are noted above, i.e., the methods described by Furukawa et al, Roth et al and Benau et al.

If no binding of the enzyme to the acceptor moiety occurs (i.e., the assay of the eluate fails to reveal the presence of glycosyltransferase(s) therein), then it can be concluded that the mixture did not contain an enzyme specific for the particular acceptor. Other mixtures of, for example, animal and/or plant cell homogenates are then contacted with the acceptor moiety until enzyme binding is observed.

When the acceptor moiety is bound by an enzyme, the species are separated and further studied. In a preferred embodiment, the acceptor and the candidate enzyme are again contacted, this time in the presence of a donor moiety which comprises the saccharide unit desired to be transferred to the acceptor moiety. If such contacting results in the transfer of the saccharide unit to the acceptor, the enzyme is a glycosyltransferase useful in the practice of this invention.

It will be appreciated that once the glycosyltransferase is identified, it can be sequenced and/or replicated by techniques well-known to those skilled in the art. For example, replication might be accomplished by recombinant techniques involving the isolation of genetic material coding for the glycosyltransferase and the preparation of an immortal cell line capable of producing the glycosyltransferase. Replication will likely prove desirable for commercial scale production of saccharide compositions in accordance with this invention.

After the glycosyltransferase is identified, it is contacted with the acceptor moiety and donor moiety under conditions sufficient to effect transfer and covalently bonding of the saccharide unit to the acceptor moiety. It will be appreciated that the conditions of, for example, time, temperature, and pH appropriate and optimal for a particular saccharide unit transfer can be determined by one of skill in the art through routine experimentation. Certain co-reagents may also prove useful in effecting such transfer. For example, it is preferred that the acceptor and donor moieties be contacted with the glycosyltransferase in the presence of divalent cations, especially manganese cations such as may be provided by $MnCl_2$.

In a preferred embodiment, the glycosyltransferase is immobilized by attachment to a solid support and the acceptor and donor moieties to be contacted therewith are added thereto. As discussed above, the glycosyltransferase used in accordance with the present invention is frequently a mixture of glycosyltransferases containing at least one glycosyltransferase possessing the desired activity, but purified single glycosyltransferases may also be used in accordance with the present invention. In this preferred embodiment, either the mixture of glycosyltransferases or the purified single glycosyltransferase may be immobilized. Alternatively, the glycosyltransferase, donor and acceptor are each provided in solution and contacted as solutes.

A preferred procedure for immobilization of glycosyltransferases—and of acceptor moieties, where necessary—is based on the copolymerization in a neutral buffer of a water soluble prepolymer such as poly (acrylamide-co-N-acryloxysuccinimide (PAN), a cross-linking diamine such as triethylenetetramine, and the glycosyltransferase, as disclosed by Pollack et al., *J. Am. Chem. Soc.* (1980) 102:6324–36. The immobilization of the enzymes on PAN is useful because small amounts of enzyme can be used, high yields of enzyme activity are obtained, and the bond between enzyme and polymer is stable.

More preferred methods of immobilization include immobilization of the glycosyltransferase amino groups onto solid support oxirane groups (see, e.g., Chun et al, *Enzyme Eng.* (1980) 5:457–460) or onto cyanogen bromide activated "SEPHADEX" or "SEPHAROSE" (Axen et al, *Nature* (1967) 214:1302–1304).

In a preferred embodiment, the glycosyltransferase is immobilized from a moderately purified composition containing the glycosyltransferase. Extremely pure enzyme preparations (ie, with specific activities in the range of 1 nMole transferred per $\mu$g protein per minute of incubation) are less efficiently immobilized covalently to solid supports, in that the percent derivatization is lower, compared to 10 or 100 times less pure preparations.

It will be appreciated that impairment of the active sites of the glycosyltransferase due to immobilization should be avoided. The inventor observed that contaminating enzyme activities tend to disappear during the immobilization process as compared to the activity of the glycosyltransferase of interest which is specifically protected during the immobilization process. During the immobilization process the glycosyltransferase may be protected by the cation required by the enzyme, the nucleotide recognized by the enzyme, and the acceptor recognized by the enzyme. For example, a galactosyl transferase may be protected with $Mn^{2+}$, N-acetylglucosamine and UDP during the immobilization, regardless of which immobilization method is used. In this way, contaminating proteases are not protected in any way during the immobilization process.

Because only the desired glycosyltransferase is protected during the immobilization process, enzymes that interfere with the synthesis of the target saccharide composition tend to be lost. Examples of interfering enzymes are proteases, which would otherwise attack the desired glycosyltransferase, and glycosidases, which would otherwise attack the product saccharide.

As noted above, in accordance with the invention, a saccharide composition prepared by contacting an acceptor moiety with a donor moiety and a glycosyltransferase can, in turn, serve as an acceptor moiety for isolating further enzymes and as an acceptor moiety to which subsequent saccharide units may be transferred. The addition of saccharide units to saccharide compositions prepared by such contact is preferred for the synthesis of carbohydrates and saccharide chains having greater than about three saccharide units.

For example, in preparing the trisaccharide N-acetylneuraminyl $\alpha$ 2-3 galactosyl $\beta$ 1-4 N-acetylglucosamine, the disaccharide galactosyl $\beta$ 1-4 N-acetylglucosamine is prepared according to this invention and then employed as an acceptor moiety to which a subsequent unit is added. Those skilled in the art will appreciate that the saccharide units attached to the saccharide compositions of this invention can be the same or different.

The saccharide compositions of this invention find use in an exceedingly wide variety of applications and may be used in the same manner as saccharide compositions available from known sources. It is preferred that the saccharide compositions be employed in therapeutic and preventative treatments for mammals, such as disclosed in U.S. Ser. No. 07/241,012, now abandoned.

The saccharide compositions of this invention are expected to find use as blocking agents for cell surface receptors in the treatment of numerous diseases of viral, bacterial, or fungal origins, such as pneumonia, candidiasis, urinary tract infections, periodontal disease, and diarrhea. For example, oligosaccharides prepared according to this invention may inhibit the attachment of pathogens such as pneumonia-causing bacteria to mammalian membrane molecules. Such pathogens might be incubated with cellular glycoproteins and glycolipids that have been separated by chromatography or electrophoresis. After detecting specific adherence patterns, the target compound could be analyzed and inhibitory saccharide composition prepared. If either of the complimentary molecules functions through its saccharide component, then specific saccharide compositions should inhibit attachment.

The saccharide compositions which can be prepared in accordance with the invention can be used in the following applications:

1. Nutritional supplements:
   infant formulas

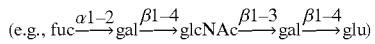

geriatric formulas
   special care formulas

2. Antibacterials:
   pneumonia

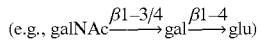

urinary tract infection

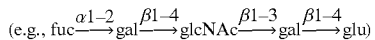

dental carries

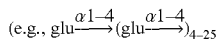

periodontal disease

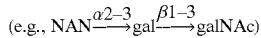

diarrhea

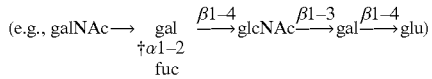

surgical (nosocomial) infections
   catheter-associated infections

3. Antitumor:
   solid tumor metastases

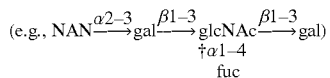

4. Anti-inflammatory:
   neutrophil-platelet interactions
   WBC-endothelium interactions
5. Naval drag-reduction:
   ship hulls
6. Contraceptives

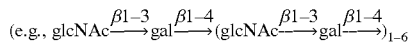

foam and jelly components
7. Antivirals:
   Herpes
   influenza
   HIV
8. Antifungals and yeasts
   oral and vaginal candidiasis (e.g., glucomannan complex, $\alpha$-D-MAN(1-6)$_n$ branched $\alpha$-(1-2) with L-RHAM, D-Gal,

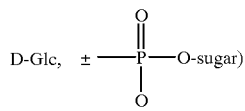

actinomycetes
9. Food additives:

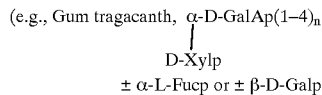

emulsifiers
   thickeners

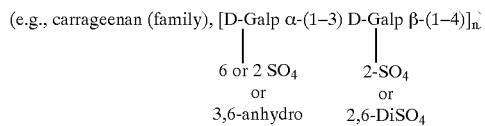

10. Veterinary:
    antibacterial
    antiviral
    antifungal
    anti-inflammatory The present invention thus also provides pharmaceutical and other compositions, such as foodstuff compositions, containing saccharide compositions prepared in accordance with the present invention. In both the pharmaceutical compositions and the foodstuff compositions provided by the invention, the saccharide composition of the invention may be present in an amount of from $10^{-3}$ $\mu$g ml$^{-1}$ to 100 mg ml$^{-1}$.

The concentration of the saccharide composition of the present invention in any given particular pharmaceutical composition or foodstuff composition will vary in terms of the activity of the saccharide being used. For pharmaceutical compositions the concentration of saccharide present in the composition will depend on the in vitro activity measured for any given compound. For foodstuff compositions, the concentration of the saccharide composition of the present invention may be determined measuring the activity of the compound being added.

For example, mother's milk contains the saccharide composition set forth above where it is indicated as being useful both in infant formula and as an antibacterial for fighting urinary tract infections. As such, the present invention provides an improvement in commercial infant formulas by permitting the addition to these commercial infant formulas the saccharide composition illustrated above. The particular saccharide composition illustrated above may be present in the commercial infant formula in an amount of 0.1 $\mu$g per ml to 1000 $\mu$g per ml. It is present in mother's milk at ca. 10 $\mu$g per ml.

The pharmaceutical compositions should be pyrogen free. Pharmaceutical compositions in accordance to the present invention may be prepared as is known in the art so as to be suitable for oral, intravenous, intramuscular, rectal, transdermal or nasal (e.g., nasal spray) administration. It may also be prepared for topical administration in the form of creams, ointments, suspensions, etc.

A few saccharides have been noted as being important both as commodity chemicals in the food, textile, and petroleum industries, and as specialty chemicals, primarily in the medical field. To date, the absence of an efficient process for preparing saccharide compositions has made it impossible to obtain commercial compositions containing, as an active ingredient, a saccharide composition.

The present invention makes such saccharide compositions readily available in large quantity for the first time. With the method of the present invention, saccharide compositions heretofore available only in miniscule quantities, and saccharide compositions heretofore unavailable, are readily made in gram and kilogram quantities. The purity of the saccharide compositions provided in accordance to the present invention exceeds 95 wt. %. In some applications requiring a high level of purity, the method of the present invention can be used to obtain saccharide compositions containing purity levels of from 98 wt. % to essentially 100 wt. %.

The present invention thus now provides for the first time pharmaceutical compositions and other compositions containing saccharide compositions of the present invention present in an effective amount. The present invention provides compositions containing the saccharide compositions obtained in accordance with the present invention present in the amount of at least 100 mg, preferably at least 500 mg, and up to 95 wt. % of the composition.

In another embodiment, the present invention provides an apparatus suitable for use in accordance with the present invention for the glycosyltransferase catalyzed synthesis of a saccharide composition. Illustrative configurations for such apparatus are provided in FIGS. 1, 2 and 3.

In a very basic embodiment the apparatus of the present invention contains one reaction chamber in which all of the glycosyltransferases, all the preselected saccharide units and the initial acceptor moiety are combined. Due to the specificity of the glycosyltransferases, this mixture, given sufficient time, will produce the saccharide composition of the present invention.

Figure 2:
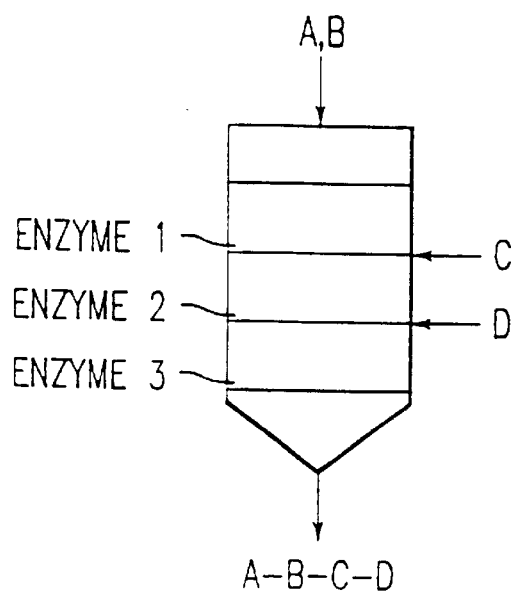
Figure 3:
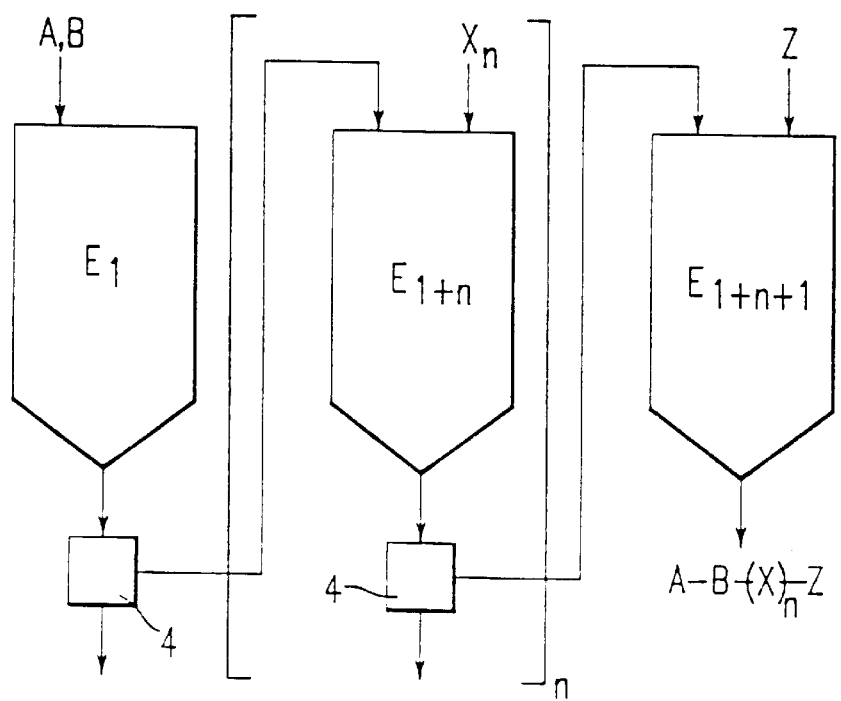

FIGS. 1, 2 and 3 illustrate more efficiently designed apparatuses which may be used in accordance with the present invention. The apparatuses illustrated in the figures, comprise, as their basic elements, a reactor equipped with an inlet and an outlet. The reactor is suitable for carrying out the sequential covalent bonding of a plurality of preselected saccharide units onto an acceptor moiety, catalyzed by a plurality of corresponding glycosyltransferases specific to each covalent bonding. It contains at least three, preferably four, and even more preferably a number greater than four, such as five, six, seven, or more, different, glycoltransferases which are preferably immobilized.

The inlet means is suitable for introducing the acceptor moiety and the plurality of preselected saccharide units into the reactor such that the saccharide composition is synthesized. Preferably, the inlet means is suitable for also introducing into the reactor the glycosyltransferases which are themselves preferably immobilized. The outlet means permits discharging the saccharide composition from the reactor.

FIG. 1 illustrates a column-type reactor charged with a solid support matrix. The various glycosyltransferases (enzymes 1, 2, 3) used in the process may be either randomly distributed throughout the solid support matrix or they may be arranged in zones as illustrated in FIG. 1. The initial acceptor moiety (shown as A in the figures) and the preselected saccharide units (shown as B, C and D in the figures) are charged into the reactor via the inlet means and passed through the solid support matrix whereupon the saccharide composition is produced due to the action of the specific glycosyltransferases and recovered via the outlet means as molecule A-B-C-D.

In the embodiment illustrated in FIG. 2, the initial acceptor moiety and the preselected saccharide unit to be attached to the initial acceptor moiety are charged at the top of the solid support matrix, with the glycosyltransferases specific to the addition of each preselected saccharide units being arranged in corresponding zones along the direction of flow of the reaction mixture. The various preselected saccharide units are then individually added at correspondingly appropriate locations along the flow of the reaction mixture as shown in the figure.

In another preferred embodiment, illustrated in FIG. 3, the reactor comprises a plurality of (n) reaction zones serially connected so as to be in sequential fluid communication with each other where (n) roughly corresponds to not more than the number of saccharide units being attached. Each reaction zone contains at least one glycosyltransferase specific to catalyze the bonding of a particular preselected saccharide unit onto the intermediate product formed in the preceding reaction zone.

In accordance with this embodiment the initial acceptor moiety (A) and the first preselected saccharide unit (B) to be attached to the acceptor moiety are passed through the first reaction zone which comprises a glycosyltransferase specific to catalyze the bonding of the first preselected saccharide unit onto the initial acceptor moiety thus producing a first intermediate product. This first intermediate product is then transferred to the second reaction zone (n=1) where it is combined with the second preselected saccharide unit $(X_n)$ and the glycosyltransferase $(E_{1+n})$ specific to catalyze the bonding of the second preselected saccharide unit with the first intermediate product formed. This process is repeated in a corresponding number of reaction zones until the target saccharide composition provided by the invention and illustrated as A-B-$(X)$-$_n$Z, wherein each X moiety is independently selected and n is an integer of from 1 to 500 or more, is obtained.

In another preferred embodiment, also illustrated in FIG. 3, means for purifying 4 each intermediate product formed from the reaction mixture emanating from any given reaction zone are situated in fluid communication and between each of the reaction zones. The means for purifying, which may comprise, e.g., an ion exchange resin, remove contaminants in the reaction mixtures which inhibit the efficiency of the bonding of the next preselected saccharide unit onto the intermediate product formed.

Additional objects, advantages, and novel features of this invention will become apparent to those skilled in the art upon examination of the following examples thereof, which are not intended to be limiting.

EXAMPLE 1

Preparation of the Trisaccharide N-Acetylneuraminyl α 2-3 Galactosyl β 1-4 N-Acetylglucosamine:

To each of five test tubes was added 10 μl of pH 7.4 potassium phosphate buffer, 10 μl of 50 MM $MnCl_2$, 17,000 CPM of cytidine monophosphate-[$^{14}C$]-N-acetyineuraminic acid, 25 μl of galactosyltransferase, and 25 μl of N-acetyineuraminyltransferase. The glycosyltransferases were purified from bovine colostrum by SEPHADEX™ G-100 gel chromatography SEPHADEX™ is a beaded gel prepared by cross-linking dextran with epichlorohydrin under alkaline conditions.

To test tube 1 was also added 10 μl of 40 mm uridine diphosphate galactose and 10 μl of 40 mM N-acetylglucosamine. Test tube 1 was incubated in ice for one hour.

To test tube 2 was also added 10 μl of 40 mM uridine diphosphate galactose. Test tube 2 was incubated at 37° C. for one hour.

To test tube 3 was also added 10 μl of 40 mM N-acetyllactosamine. Test tube 3 was incubated at 37° C. for one hour.

To test tubes 4 and 5 were also added 10 μl of 40 mM uridine diphosphate galactose and 10 μl of 40 mM N-acetylglucosamine. Test tubes 4 and 5 were incubated at 37° C. for one hour.

After incubation, the contents of the test tubes were each subjected to high voltage electrophoresis on paper saturated with sodium tetraborate. Isotopically labeled trisaccharide product was identified by its mobility, as demonstrated by the product formed in test tube 3.

| Test Tube | Trisaccharide (cpm) |
| --- | --- |
| 1 | 0 |
| 2 | 0 |
| 3 | 3375 |
| 4 | 670 |
| 5 | 954 |

As can be seen, the presence of suitable acceptor moieties, donor moieties, and glycosyltransferases in test tubes 4 and 5 yielded the expected trisaccharide product from monosaccharide starting materials. Typically, the sialic acid N-acetylneuraminate presents special problems for synthetic organic chemists seeking to incorporate it into saccharide compositions, due to the acid lability of its glycosidic bond. Synthesizing a trisaccharide from cytidine monophosphate N-acetylineuraminic acid enzymatically eliminates the synthetic problems associated with removing protecting groups under strong acidic condition.

It is believed that an acceptor moiety (N-acetylglucosamine) initially contacts a donor moiety (uridine diphosphate galactose) and a glycosyltransferase (galactosyltransferase) to produce a saccharide composition (galactosyl β 1-4 N-acetylglucosamine), which then acts as an acceptor moiety upon contacting a second donor moiety (cytidine monophosphate N-acetylneuraminic acid) and a second glycosyltransferase (N-acetylneuraminyltransferase).

The synthesis of the trisaccharide product in test tubes 4 and 5 from monosaccharide starting materials is confirmed by comparison with the product of test tube 3, in which the trisaccharide is formed by contacting a disaccharide acceptor moiety (N-acetyllactosamine) with cytidine monophosphate N-acetylneuraminic acid and N-acetylneuraminyltransferase.

The absence of trisaccharide in test tube 2 illustrates that a suitable acceptor moiety is necessary for trisaccharide formation. The absence of trisaccharide in test tube 1 indicates that the synthesis of the trisaccharide is, indeed, dependent upon the action of any enzyme (the glycosyltransferase) that is inactive at low temperatures.

It is expected that the oligosaccharides N-acetylgalactosaminyl α 1-3 (fucosyl α 1-2) galactosyl β 1-4 N-acetylglucosaminyl β 1-3 galactose (a target for diarrhea-causing bacteria) and N-acetylgalactosaminyl β 1-4 galactosyl β 1-4 glucose (a target for pneumonia-causing bacteria) can likewise be prepared by the processes of the present invention.

EXAMPLE 2

Tetrasaccharide Biosynthesis Protocol

Enzymes:

N-acetylglucosaminyltransferase:

Human colostrum is centrifuged for one hour at 70,000× G. A 25% saturated ammonium sulfate cut yields a supernatant that is dialyzed to remove the ammonium sulfate. The retentate is applied to a SEPHADEX™ G-200 column (2.5×83 cm). The protein profile is determined spectrophotometrically at 280 nm, and a radioactive assay is performed to locate the fractions with transferase activity. The fractions containing the single enzyme peak are pooled and concentrated 10-fold by Amicon filtration. The pooled enzyme preparation is again assayed, and the protein concentration is determined using a BioRad assay. The specific activity of the preparation is 5.3 pMoles per µg protein-min.

Galactosyltransferase:

Human colostrum is centrifuged at 8700×G for 15 minutes. The supernatant is poured through cheesecloth and 10 ml is applied to a SEPHADEX™ G-100 column (2.5×90 cm). The protein profile is determined spectrophotometrically at 280 nm, and a radioactive assay is performed to locate the fractions with enzyme activity. The fractions with the highest activity are pooled and concentrated 10-fold by Amicon filtration. The pooled enzyme preparation is again assayed, and the protein concentration is determined as above. The specific activity of the preparation is 15.4 pMoles per µg protein-min.

Enzyme Immobilization:

N-acetylglucosaminyltransferase:

300 mgs of Eupergit beads (1.2 ml) are washed three times with deionized water, and then three times with aseptic Hepes-buffered water. One ml of the enzyme preparation is combined aseptically with the beads along with UDP, lactose, MnCl$_2$, (final concentrations: 10, 25, and 10 mM, respectively) and a drop of chloroform in a Hepes-buffered solution. The beads are gently agitated at 4° C. for 2½ days. Aliquots are taken and assayed periodically. To stop the derivatization, the beads are washed three times with an aseptic buffer, and stored in buffer, in the cold, with UDP, lactose, MnCl$_2$, and chloroform.

Galactosyltransferase:

3.75 grams of beads are washed three times with deionized water, and then three times with aseptic Hepes-buffered water. The beads are added to 3-mls of the enzyme preparation (in both cases, optimum derivatization occurs at about 1 mg protein per 200 mgs beads) along with UDP, GlcNAc, MnCl2, (final concentrations are all 10 mM) and a drop of chloroform in a Hepes-buffered solution. Derivatization and storage are as described above, except that the GlcNac is used with the galactosyltransferase in place of lactose, which is the acceptor for the N-acetylglucosaminyltransferase.

Tetrasaccharide Production:

Derivatized N-acetylglucosaminyltransferase (0.5 ml beads) is incubated under constant stirring with lactose (25 mM), UDPGlcNAc (80 µM), and MnCl$_2$ (10 mM) for 21 hours. This incubation is carried out in duplicate-the supernatant of one incubation is used to measure the amount of trisaccharide produced (14 µg), and the supernatant from the other incubation is added to 0.5 ml beads derivatized with the galactosyltransferase. The galactosyltransferase incubation contains, therefore, 14 µg of trisaccharide, 25 µM UDPgal, and 10 mM MnCl$_2$. After 24 hours at room temperature, the second enzyme preparation produces about 1.6 µg of tetrasaccharide. After 31 hours, 2.2 µg of tetrasaccharide were produced.

EXAMPLE 3

The following schemes will be used for synthesizing three, relatively complex oligosaccharides: the A- and B-type milk oligosaccharides (I and II), and gum tragacanth (III), a plant oligosaccharide used by the ton as a food additive.

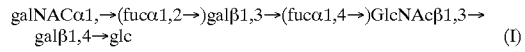

galNACα1,→(fucα1,2→)galβ1,3→(fucα1,4→)GlcNAcβ1,3→galβ1,4→glc    (I)

First, the hexanolamine glycoside (glc-O—(CH$_2$)$_6$—NH$_2$) of glucose that will be affixed to CNBr-activated supports, e.g., SEPHAROSE™, a beaded agarose, via the amino group of the hexanolamine will be synthesized. Then the glucose-recognizing galactosyltransferase will be purified from human milk or colostrum using this affinity ligand. The enzyme, once partly purified, will be used to galactosylate glucose, making lactose.

Alternatively, the hexanolamine glycoside of lactose, which is an inexpensive and readily available disaccharide, will be synthesized. The lactose so produced will be attached to SEPHAROSE™ and used as an affinity ligand to purify in part the N-acetylglucosaminyltransferase from human colostrum, or from human plasma.

Next, this second transferase will be used to add N-acetylglucosamine to lactose, making the trisaccharide, which will again be attached to SEPHAROSE™. This bound trisaccharide will be used to obtain the β1,3 galactosyltransferase (from porcine submaxillary gland), which will, in turn, yield the substrate for purifying the next enzyme—the α1,4 fucosyltransferase (from porcine liver). The α1,2 fucosyltransferase (from porcine submaxillary gland), and, finally, the α1,3 N-acetylgalactosaminyltransferase (from porcine submaxillary glands) that terminates the synthesis of the A-type milk oligosaccharide will be affinity purified in this step-wise fashion. Each transferase so obtained will be immobilized to a solid matrix by any of several means, and the matrices will be poured in column configurations.

The enzyme-containing columns will be used sequentially, in the same order that the smaller amounts of derivatized substrates were synthesized, to synthesize large amounts each soluble oligosaccharide.

The order of attachment of the sugars is critical. The proximal fucose (that attached α1,4 to glcNAc) must be attached to the completed core tetrasaccharide before the addition of the second fucose (that attached α1,2 to the galactose. Finally, the terminal galNAc (α1,3) is added to complete the seven-sugar oligosaccharide. This order is required by the specificities of the glycosyltransferases.

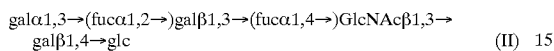
galβ1,4→glc (II)

Having synthesized I, II will be synthesizes in precisely the same fashion, except that the hexasaccharide will be used, first, to purify an α1,3 galactosyltransferase that will be derivitized with protective groups for a galactosyl-, and not an N-acetylgalactosaminyltransferase. This enzyme will then be used to synthesize the B-type oligosaccharide.

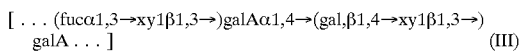
galA . . . ] (III)

To isolate the enzyme that synthesizes the α1,4 galacturonic acid backbone of gum tragacanth, which currently is available only from the bark of a tree species indigenous to the Middle East, hexagalacturonans will be prepared from pectin, a common constituent of citrus rinds, and used as an affinity ligand.

The same affinity ligand can next be used to isolate from tree tissues the xylosyltransferase that synthesizes the proximal β1,3 xylosides. The xylosylated galacturonans, once derivatized, will be used to isolate both the fucosyl- and galactosyltransferases that, respectively, fucosylate and galactosylate the xylosylated galacturonan. In the case of this oligosaccharide, the degree of xylosylation, fucosylation, and galactosylation will be controlled empirically by the number of passes of the compounds through the appropriate enzyme-containing columns. The number of repeat units produced will depend on the number of galacturonic acid residues used initially; this number will vary in length from four to twenty monosaccharide units.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for the synthesis of a preselected saccharide composition, comprising:
   (a) contacting a preselected acceptor moiety which is a carbohydrate and at least two preselected saccharide donor moieties with at least two isolated glycosyltransferases, wherein each of said glycosyltransferases catalyzes formation of a specific stereochemical linkage, wherein
      (i) one of said glycosyltransferases catalyzes the transfer of the saccharide unit of one of said saccharide donor moieties to said preselected acceptor moiety to form an intermediate product, and
      (ii) the other glycosyltransferase catalyzes the transfer of the saccharide unit of another one of said saccharide donor moieties to said intermediate product, thereby forming said preselected saccharide composition; and
   (b) recovering said preselected saccharide composition, wherein
      (i) one of said glycosyltransferases is specific only for said preselected acceptor moiety and one of said preselected saccharide donor moieties, and
      (ii) the other glycosyltransferase is specific only for said intermerdiate product and another of said preselected saccharide donor moieties, further wherein said isolated glycosyltransferases are obtained by a method comprising:
   (c) contacting an acceptor moiety which is a carbohydrate immobilized on a solid or semi-solid support with a mixture of glycosyltransferases under conditions suitable to effect bonding of the glycosyltransferases specific for the acceptor moiety, thereby forming immobilized acceptor moiety-glycosyltransferase complexes;
   (d) isolating one of said glycosyltransferases by eluting said glycosyltransferase from the immobilized complexes by contacting the immobilized complexes with a donor moiety comprising a preselected saccharide unit under conditions suitable to effect the glycosyltransferase-catalyzed transfer of the preselected saccharide unit from the donor moiety to the immobilized acceptor moiety, thereby releasing said glycosyltansferase and fornng an immobilized intermediate product;
   (e) collecting the released glycosyltransferase; and
   (f) repeating steps (c), (d) and (e) at least once such that each time said steps are repeated, the immobilized intermediate product obtained in step (d) functions as the acceptor moiety of step (c),
   wherein at least one donor moiety is a saccharide nucleotide selected from the group consisting of a saccharide-terminated uridine phosphate, a saccharide-terminated guanosine phosphate and a saccharide-terminated cytidine phosphate, and wherein at least one acceptor moiety is selected from the group consisting of glucose, galactose, lactose, N-acetylglucosamine, N-acetylgalactosamine, N-acetyllactosamine and galactosyl β1-4 N-acetylglucosamine.

2. The method of claim 1, wherein the carbohydrate is selected from the group consisting of a monosaccharide, a disaccharide, an oligosaccharide, and a polysaccharide.

3. The method of claim 1, wherin the saccharide-terminated uridine phosphate is uridine diphosphate galactose.

4. The method of claim 1, wherein the saccharide-terminated cytidine phosphate is cytidine monophosphate N-acetylneuraminic acid.

5. The method of claim 1, wherein at least one glycosyltransferase is a galactosyltransferase.

6. The method of claim 1, wherein at least one glycosyltransferase is a N-acetylneuraminyltransferase.

7. The method of claim 1, wherein said carbohydrate in step (c) is immobilized on a solid support.

8. The method of claim 1, wherein said carbohydrate in step (c) is immobilized on a semi-solid support.

9. The method of claim 1, wherein at least one donor moiety is saccharide-terminated uridine phosphate.

10. The method of claim 1, wherein at least one donor moiety is saccharide-terminated guanosine phosphate.

11. The method of claim 1, wherein at least one donor moiety is saccharide-terminated cytidine phosphate.

12. The method of claim 1, wherein at least one donor moiety is a saccharide nucleotide selected from the group consisting of a saccharide-terminated uridine phosphate and a saccharide-terminated guanosine phosphate.

13. The method of clain 1, wherein at least one acceptor moiety is glucose.

14. The method of clain 1, wherein at least one acceptor moiety is galactose.

15. The method of clain 1, wherein at least one acceptor moiety is lactose.

16. The method of clain 1, wherein at least one acceptor moiety is N-acetylglucosamine.

17. The method of clain 1, wherein at least one acceptor moiety is N-acetylgalactosamine.

18. The method of clain 1, wherein at least one acceptor moiety is N-acetyllactosamine.

19. The method of clain 1, wherein at least one acceptor moiety is galactosyl β1-4 N-acetylglucosamine.

20. The method of claim 2, wherein the carbohydrate is a monosaccharide.

21. The method of claim 2, wherein the carbohydrate is a disaccharide.

22. The method of claim 2, wherein the carbohydrate is an oligosaccharide.

23. The method of claim 2, wherein the carbohydrate is a polysaccharide.

* * * * *